United States Patent
Liu et al.

(10) Patent No.: US 11,103,211 B2
(45) Date of Patent: *Aug. 31, 2021

(54) ULTRASONIC MEDICAL MONITORING DEVICE AND METHOD

(71) Applicant: SHENZHEN MINDRAY BIO-MEDICAL ELECTRONICS CO., LTD., Shenzhen (CN)

(72) Inventors: Yang Liu, Shenzhen (CN); Xiaocui Zhang, Shenzhen (CN); Yi Han, Shenzhen (CN); Shuo Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/899,222

(22) Filed: Jun. 11, 2020

(65) Prior Publication Data

US 2020/0297314 A1    Sep. 24, 2020

Related U.S. Application Data

(63) Continuation of application No. 15/199,171, filed on Jun. 30, 2016, now Pat. No. 10,716,538, which is a
(Continued)

(51) Int. Cl.
*A61B 8/00* (2006.01)
*A61B 8/06* (2006.01)
(Continued)

(52) U.S. Cl.
CPC ........ *A61B 8/4416* (2013.01); *A61B 5/02108* (2013.01); *A61B 5/02152* (2013.01);
(Continued)

(58) Field of Classification Search
CPC ..... A61B 8/4416; A61B 8/065; A61B 8/4477; A61B 5/02108
See application file for complete search history.

(56) References Cited

U.S. PATENT DOCUMENTS 6,340,349 B1 * 1/2002 Archibald .......... A61B 5/02116
                                                        600/494
2002/0128554 A1   9/2002 Seward
(Continued)

FOREIGN PATENT DOCUMENTS

CN    101031242 A    9/2007
CN    101119680 B    2/2008
(Continued)

OTHER PUBLICATIONS

Garcia et al., "Dynamic arterial elastance to predict arterial pressure response to volume loading in preload-dependent patients", Critical Care201115:R15, https://ccforum.biomedcentral.com/articles/10.1186/cc9420, published Jan. 12, 2011, viewed on Jan. 31, 2019.*
(Continued)

*Primary Examiner* — Allen Porter
*Assistant Examiner* — James Moss
(74) *Attorney, Agent, or Firm* — Kory D. Christensen

(57) ABSTRACT

An ultrasonic medical monitoring device may include: at least one ultrasonic probe that scans a test subject to acquire an echo signal; a blood pressure measuring device that measures a blood pressure parameter of a peripheral artery of the test subject; a processor configured to receive the echo signal and process the echo signal to obtain a blood flow parameter, and to calculate a myocardial mechanic parameter that represents a synchronous coupling of a circulatory system of left ventricle-aorta-peripheral arteries circulation according to the blood flow parameter and the blood pres-
(Continued)

sure parameter; and a display device that is coupled to the processor and displays the myocardial mechanic parameter.

15 Claims, 3 Drawing Sheets

Related U.S. Application Data continuation of application No. PCT/CN2014/071403, filed on Jan. 24, 2014.

(51) Int. Cl.
*A61B 8/04* (2006.01)
*A61B 5/021* (2006.01)
*A61B 5/0215* (2006.01)
*A61B 5/022* (2006.01)
*A61B 8/08* (2006.01)
*A61B 8/14* (2006.01)

(52) U.S. Cl.
CPC ............ *A61B 5/02241* (2013.01); *A61B 8/04* (2013.01); *A61B 8/06* (2013.01); *A61B 8/5223* (2013.01); *A61B 8/065* (2013.01); *A61B 8/14* (2013.01); *A61B 8/42* (2013.01); *A61B 8/4477* (2013.01); *A61B 8/463* (2013.01); *A61B 8/485* (2013.01); *A61B 8/488* (2013.01); *A61B 2560/0475* (2013.01)

(56) References Cited

U.S. PATENT DOCUMENTS

| | | | | |
|---|---|---|---|---|
| 2007/0197921 | A1* | 8/2007 | Cohen | A61B 5/02116 |
| | | | | 600/485 |
| 2007/0276196 | A1* | 11/2007 | Donaldson | A61B 5/0002 |
| | | | | 600/300 |
| 2008/0119741 | A1* | 5/2008 | Friedman | A61B 5/02007 |
| | | | | 600/485 |
| 2011/0009754 | A1* | 1/2011 | Wenzel | A61B 5/0215 |
| | | | | 600/485 |
| 2011/0270089 | A1* | 11/2011 | Vezina | A61B 5/02028 |
| | | | | 600/443 |
| 2013/0245441 | A1* | 9/2013 | Datta | A61B 8/13 |
| | | | | 600/438 |
| 2014/0071069 | A1 | 3/2014 | Anderson et al. | |
| 2014/0121524 | A1 | 5/2014 | Chiang et al. | |
| 2016/0029995 | A1* | 2/2016 | Navratil | A61B 8/0891 |
| | | | | 600/301 |

FOREIGN PATENT DOCUMENTS

| | | |
|---|---|---|
| CN | 101365387 A | 2/2009 |
| CN | 102753101 A | 10/2012 |
| CN | 202776368 U | 3/2013 |
| CN | 202932946 U | 5/2013 |

OTHER PUBLICATIONS

Matthew Hoffman, "Picture of the Aorta", https://web.archive.org/web/20131122050751/https://www.webmd.com/heart/picture-of-the-aorta, Way Back Machine Capture on Nov. 22, 2013, viewed on Jan. 29, 2019).*

"Cardiovascular Physiology: Integrative Function | Anesthesia Key", https://aneskey.com/cardiovascular-physiology-integrative-function/, viewed on Sep. 11, 2019, fig. 24.6 is reprinted from Ganong WF. Review of Medical Physiology. Norwalk, CT: Appleton & Lange; 1987:467.*

Garcia et al., "Dynamic arterial elastance to predict arterial pressure response to volume loading in preload-dependent patients", Critical Care201115:R15, https://ccforunbiornedcentral.corn/articles/10.1186/cc9420, published Nov. 12, 2011, viewed on Jan. 31, 2019.

Matthew Hoffman, "Picture of the Aorta", https://web.archive.org/web/20131122050751/https://www.webrnd.corn/heart/ picture-of-the-aorta, Way Back Machine Capture on Nov. 22, 2013, viewed on Jan. 29, 2019).

* cited by examiner

ULTRASONIC MEDICAL MONITORING DEVICE AND METHOD

CROSS-REFERENCE TO RELATED APPLICATIONS

This application is a continuation of U.S. application Ser. No. 15/199,171, filed Jun. 30, 2016, for ULTRASONIC MEDICAL MONITORING DEVICE AND METHOD, which is a continuation of PCT Application No. PCT/CN2014/071403, filed Jan. 24, 2014, both of which are incorporated herein by reference.

FIELD OF THE INVENTION

The present disclosure relates to medical equipment, and more particularly relates to a multi-probe synchronous scanning ultrasonic medical monitoring device and method.

BACKGROUND OF THE INVENTION

In the ventricular-peripheral arterial coupling, the circulatory system is considered as a whole, the ventricle and artery can be regarded as an elastic system, and the effects thereof are mutually influenced. The diastolic and systolic function of the ventricle can supply blood for internal organs, including the ventricle itself and distal limbs. Since the left ventricle and the aorta can be regarded as a driving pump and a passive pump connected in series, the resistance of the driving pump and peripheral vascular tree will be reflected in the artery waveform curve. When the ventricle and the peripheral arteries are matched and well coupled, three peaks will appear in the pulse wave, which represents the left ventricle, aorta and aortic valve closure, respectively. The rules of ventricular contraction and peripheral arterial coupling can be determined once the ventricular volume and the peripheral arteries' volume and/or pressure information are obtained simultaneously.

Among numerous cardiac function tests, index, stroke volume, and ejection fraction, etc., are influenced by cardiac preload, afterload, and heart rate; thus they cannot be used to reflect specific in vivo (contrary to "in vitro" in this context) ventricular systolic function and myocardial contractility. Plenty of data show that the end-systolic pressure-volume relation plays a significant role in assessment of systolic function status. The Maximum Elastance (E max) measured by the conventional cardiac catheterization is a slope of the ventricular end-systolic pressure-volume relation line, which is a specific index reflecting in vivo ventricular contractility. However, due to the traumatic problem and expensive price, the cardiac catheterization is difficult to carry out in clinical settings.

SUMMARY OF THE INVENTION

Accordingly, it is necessary to provide an ultrasonic medical monitoring device and method which can acquire myocardial mechanics parameters in a less invasive manner.

An ultrasonic medical monitoring device includes:
at least one ultrasonic probe attached to a body surface of a tested subject and configured to scan the body surface and acquire an echo signal;
a blood pressure measuring module configured to measure a blood pressure parameter of the tested subject;
a processing module configured to receive the echo signal and process the echo signal into a blood flow parameter, the processing module being further configured to calculate a myocardial mechanic parameter according to the blood flow parameter and the blood pressure parameter; and
a display module coupled to the processing module and configured to display the blood pressure parameter, the blood flow parameter, and the myocardial mechanic parameter.

In one embodiment, the blood pressure parameter includes peripheral arterial pulse wave information and blood pressure information.

In one embodiment, the blood pressure information includes a systolic pressure, a diastolic pressure, and a mean arterial pressure.

In one embodiment, the ultrasonic medical monitoring device includes a plurality of ultrasonic probes attached to different portions of the body surface of the tested subject.

In one embodiment, the plurality of ultrasonic probes are attached to the ventricle, aorta and peripheral arteries of the tested subject to perform synchronized real-time scanning.

In one embodiment, the processing module is configured to digitally process the echo signal to obtain a digital processing signal, and to obtain a numerical parameter, waveform or trend graph calculation according to the digital processing signal, wherein the digital processing signal is selected from the group consisting of: RF signal, baseband signal, and envelope signal.

In one embodiment, the processing module is configured to digitally process the echo signal to obtain a digital processing signal, and to obtain an ultrasound image according to the digital processing signal and a chosen imaging mode, and to obtain the blood flow parameter calculation according to the ultrasound image, wherein the imaging mode supported by the processing module is selected from the group consisting of: B-mode imaging mode, M-mode imaging mode, color imaging mode, pulsed-wave imaging mode, elastosonography mode, 3D imaging mode, and 4D imaging mode.

In one embodiment, the blood flow parameter includes at least one of 2D ventricular motion curve, M-mode ventricular motion curve, 2D or M-mode aortic motion curve, aortic forward Doppler blood flow signal, 2D or M-mode peripheral artery motion curve, and peripheral arterial Doppler flow signal.

In one embodiment, the processing module is configured to obtain at least one selected from the group consisting of: cardiac ejection fraction, left ventricular fractional shortening, stroke volume, cardiac output, cardiac index, left ventricular end-diastolic volume, and left ventricular end-systolic volume, which are calculated according to the blood flow parameter.

In one embodiment, the processing module is configured to obtain at least one selected from the group consisting of: ventricular diameter, ventricular volume, M-mode curve rising speed and acceleration, which are calculated according to the blood flow parameter.

In one embodiment, the myocardial mechanic parameter is selected from the group consisting of: duration from aortic valve closure to starting point of ABP waveform ascending branch, aortic waveform variability weighed by ventricle SV variability, slope of the ascending branch of ABP waveform regressed by M-mode curve rising speed, slope of the ascending branch of ABP waveform regressed by aortic forward blood flow velocity, X-axis intercept of left ventricular end-systolic pressure-volume relation line, and systolic maximum elastance.

In one embodiment, the systolic maximum elastance is calculated by the following formula: E max=Pes/(Ves−Vop), where E max is the systolic maximum elastance; Pes is the end-systolic left ventricular pressure; Ves is the left ventricular end-systolic volume; and Vop is the X-axis intercept of the left ventricular end-systolic pressure-volume relation line.

In one embodiment, the ultrasonic medical monitoring device further includes an operation panel configured to receive a trigger signal, wherein the display module is configured to display a plurality of display windows, and the plurality of display windows are switchable for displaying numerical parameters, a waveform, and a trend graph upon triggering of the operation panel.

In one embodiment, the blood pressure measuring module is at least one selected from the group consisting of: aneroid sphygmomanometer, finger sphygmomanometer, arterial catheter, and venous catheter tube.

In one embodiment, the ultrasonic medical monitoring device further includes a storage module configured to store the blood pressure parameter and the blood flow parameter.

An ultrasonic medical monitoring method is implemented on the ultrasonic medical monitoring device described above, and the method includes the following steps:

scanning, by an ultrasonic probe, a body surface of a tested subject to acquire an echo signal;

measuring, by a blood pressure measuring module, a blood pressure parameter of the tested subject;

receiving, by a processing module, the echo signal and processing the echo signal into a blood flow parameter, and calculating a myocardial mechanic parameter according to the blood flow parameter and the blood pressure parameter; and displaying, by a display module, the blood pressure parameter, the blood flow parameter, and the myocardial mechanic parameter.

In one embodiment, the blood pressure parameter includes peripheral arterial pulse wave information and blood pressure information.

In one embodiment, the blood pressure information includes a systolic pressure, a diastolic pressure, and a mean arterial pressure.

In one embodiment, the ultrasonic medical monitoring device further includes a plurality of ultrasonic probes attached to different portions of the body surface of the tested subject.

In one embodiment, the plurality of ultrasonic probes are attached to the ventricle, aorta and peripheral arteries of the tested subject to perform synchronized real-time scanning.

In one embodiment, processing the echo signal by the processing module includes: digitally processing the echo signal to obtain a digital processing signal, and obtaining a numerical parameter, waveform or trend graph calculation according to the digital processing signal, wherein the digital processing signal is selected from the group consisting of: RF signal, baseband signal, and envelope signal.

In one embodiment, processing the echo signal by the processing module includes: digitally processing the echo signal to obtain a digital processing signal, and obtaining an ultrasound image according to the digital processing signal and a chosen imaging mode, and obtaining the blood flow parameter calculation according to the ultrasound image, wherein the imaging mode supported by the processing module is selected from the group consisting of: B-mode imaging mode, M-mode imaging mode, color imaging mode, pulsed-wave imaging mode, elastosonography mode, 3D imaging mode, and 4D imaging mode.

In one embodiment, the blood flow parameter includes at least one of 2D ventricular motion curve, M-mode ventricular motion curve, 2D or M-mode aortic motion curve, aortic forward Doppler blood flow signal, 2D or M-mode peripheral artery motion curve, and peripheral arterial Doppler flow signal.

In one embodiment, the processing module is configured to obtain at least one selected from the group consisting of: cardiac ejection fraction, left ventricular fractional shortening, stroke volume, cardiac output, cardiac index, left ventricular end-diastolic volume, and left ventricular end-systolic volume, which are calculated according to the blood flow parameter.

In one embodiment, the processing module is configured to obtain at least one selected from the group consisting of: ventricular diameter, ventricular volume, M-mode curve rising speed and acceleration, which are calculated according to the blood flow parameter.

In one embodiment, the myocardial mechanic parameter is selected from the group consisting of: duration from aortic valve closure to starting point of ABP waveform ascending branch, aortic waveform variability weighed by ventricle SV variability, slope of the ascending branch of ABP waveform regressed by M-mode curve rising speed, slope of the ascending branch of ABP waveform regressed by aortic forward blood flow velocity, X-axis intercept of left ventricular end-systolic pressure-volume relation line, and systolic maximum elastance.

In one embodiment, the systolic maximum elastance is calculated by the following formula: $E\max=Pes/(Ves-Vop)$, where E max is the systolic maximum elastance; Pes is the end-systolic left ventricular pressure; Ves is the left ventricular end-systolic volume; and Vop is the X-axis intercept of the left ventricular end-systolic pressure-volume relation line.

In one embodiment, the display module is configured to display a plurality of display windows, and the plurality of display windows are switchable for displaying numerical parameters, a waveform, and a trend graph upon triggering of the operation panel.

In one embodiment, the blood pressure measuring module is at least one selected from the group consisting of: aneroid sphygmomanometer, finger sphygmomanometer, arterial catheter, and venous catheter tube.

In one embodiment, the method further comprises storing, by a storage module, the blood pressure parameter and the blood flow parameter.

Compared with the conventional cardiac catheterization, the foregoing device and method acquire the blood pressure parameter and the blood flow parameter using ultrasound and a blood pressure synchronous detection technique, and the myocardial mechanics parameters such as the systolic maximum elastance are calculated by a computer program; therefore, the device and method are less invasive to the human body and are suitable for clinical application.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

The above and other features of the invention, including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

Figure 1:
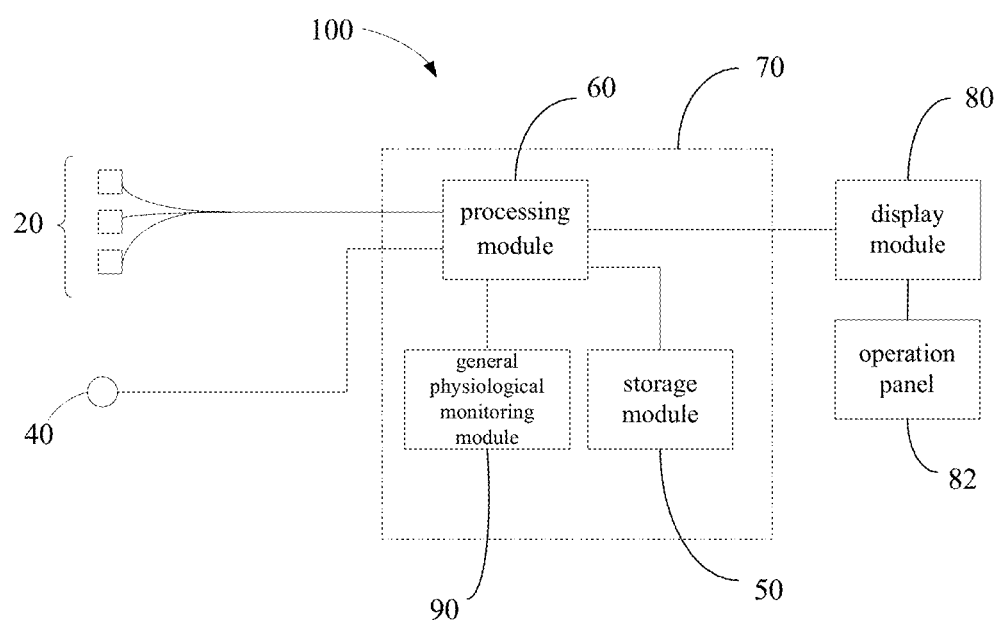
FIG. 1 is a block diagram of a schematic configuration of an ultrasound medical monitoring equipment according to an embodiment.

Referring to FIG. 1, an ultrasonic medical monitoring device 100 according to an embodiment includes at least one ultrasonic probe 20, a blood pressure measuring module 40, a processing module 60, and a display module 80.

The number of the ultrasonic probe 20 can be one or more. In one embodiment, a plurality of ultrasonic probes 20 are attached to different portions of a body surface of a tested subject (e.g., a human body) to transmit ultrasonic waves to the body tissue. The ultrasonic waves are reflected or scattered by blood vessels, and partially returned to the ultrasonic probe 20 and received by the ultrasonic probe 20 as an echo, such that a longtime, stable continuous ultrasound scan monitoring sections of different parts can be achieved. A user (e.g., a doctor) can freely adjust the fixing positions (e.g., the ventricle, aorta and peripheral arteries) of the ultrasonic probe 20 to scan the same section of the fixing position of the tested subject, such that the probes can scan the human body at any desired angle, and thus a more accurate ultrasonic image can be obtained. The echo signal acquired by scanning will be transmitted to the processing module 60 by the plurality of ultrasonic probes 20.

Figure 2:
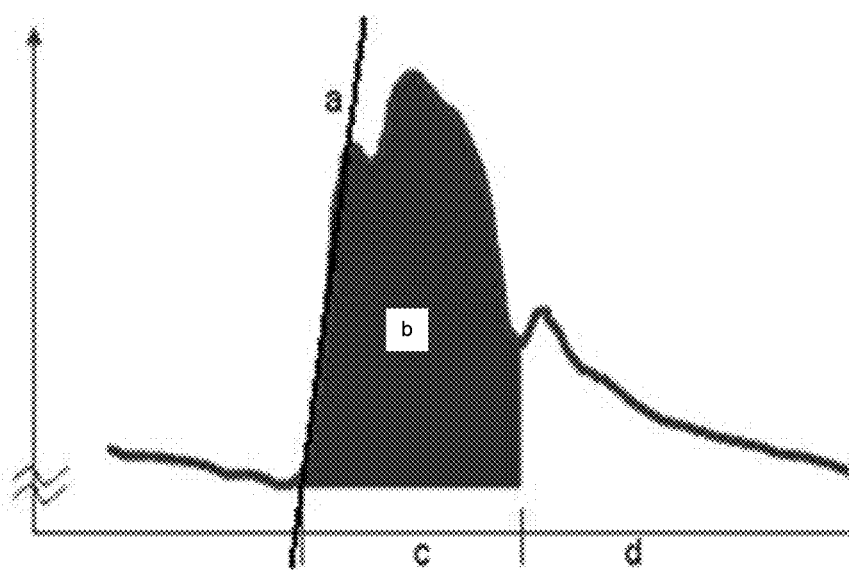
FIG. 2 is an explanatory diagram of an example in a blood pressure waveform curve.

The blood pressure measuring module 40 is mainly configured to measure a blood pressure parameter of the tested subject, and the parameter is then transmitted to the processing module 60. Measurement methods can be non-invasive or invasive. Specifically, the blood pressure measuring module 40 can be at least one of the following devices: aneroid sphygmomanometer, finger sphygmomanometer, arterial catheter, and venous catheter tube. The blood pressure measuring module 40 is wired to the processing module 60. In alternative embodiments, the blood pressure measuring module 40 can be a pressure sensor on the various principles or a pressure measuring module in other forms, including various modules employed by indirect measurement and direct measurement, such as a volume compensation method or pulse wave velocity measurement method. The blood pressure measuring module 40 can also be an ultrasonic blood pressure measurement module, which will not be described in further detail. The measured blood pressure parameter includes peripheral arterial pulse wave information and blood pressure information, such as a mean arterial pressure, a diastolic pressure, a systolic pressure, and a blood pressure waveform curve, etc. FIG. 2 illustrates a typical blood pressure waveform curve, where "a" represents a rate of pressure rise, which is related to myocardial contractility; "b" represents area under the pulse pressure curve to indicate stroke volume; "c" represents systolic period to indicate myocardial oxygen consuming time; and "d" represents a diastolic period to indicate myocardial oxygen supply time. Under the control of the processing module 60, the blood pressure measuring module 40 can perform simultaneous scanning with the plurality of ultrasonic probes 20.

The processing module 60 can be integrated into a monitoring host 70 and is configured to process the acquired echo signal to obtain a blood flow parameter. In one embodiment, processing the echo signal of the tested subject by the processing module 60 specifically includes: calculating according to the echo signal a numerical parameter, waveform or trend graph, wherein the numerical parameter is the physiological parameters of hemodynamic parameters, cardiac parameters and other information. In an alternative embodiment, processing the echo signal of the tested subject by the processing module 60 specifically includes: digitally processing the echo signal to obtain a digital processing signal, and optionally generating the selected ultrasound images or ultrasound images in supported imaging modes. The processing module 60 then performs an automatic calculation and analysis based on the obtained ultrasound images in supported imaging modes to obtain a numerical parameter, waveform or trend graph. The digital processing signal is selected from the group consisting of: RF signal, baseband signal, and envelope signal. The supported imaging modes of the processing module 60 are selected from the group consisting of: B-mode (Brightness) imaging mode, M-mode (Motion-Time) imaging mode, color imaging mode, pulsed-wave (PW) imaging mode, elastosonography mode, 3D (three-dimensional) imaging mode, and 4D (four-dimensional) imaging mode.

The obtained blood flow parameter processed by the processing module 60 can include hemodynamic parameters and cardiac parameters; for example, the blood flow parameter can include at least one of: 2D ventricular motion curve, M-mode ventricular motion curve, 2D or M-mode aortic motion curve, aortic forward Doppler blood flow signal, 2D or M-mode peripheral artery motion curve, and peripheral arterial Doppler blood flow signal. In one embodiment, on the basis of the foregoing blood flow parameters, at least one of the following parameters can be calculated by the processing module 60: cardiac ejection fraction, left ventricular fractional shortening, stroke volume, cardiac output, cardiac index, left ventricular end-diastolic volume, and left ventricular end-systolic volume. In one embodiment, at least one of the following parameters can be calculated by the processing module 60: ventricular diameter, ventricular volume, M-mode curve rising speed and acceleration.

In the illustrated embodiment, at least one of the myocardial mechanic parameters below is calculated by the processing module 60 according to said blood flow parameters and the blood pressure parameter obtained by the blood pressure measuring module 40:

(1) duration from aortic valve closure to starting point of arterial blood pressure (ABP) waveform ascending branch. The closing time of the aortic valve can be obtained by an M-mode ultrasound image; the starting time of the ABP waveform ascending branch can be obtained via the blood pressure measuring module 40; and the duration can be a difference between the closing time and the starting time.

(2) aortic waveform variability weighed by ventricle stroke volume (SV) variability. The stroke volume variability (SVV) can be calculated by the following equation: SVV=(SV max−SV min)/SVmean; i.e., the stroke volume variability can be defined as the ratio of difference between the maximum stroke volume (SV max) and the minimum stroke volume (SV min) to the average of stroke volume (SVmean). With reference of the pulse pressure variation (PPV), the aortic waveform variability can be calculated by the following equation: PPV=(PP max−PP min)/PPmean, where the maximum pulse pressure (PP max) and the minimum pulse pressure (PP min) can be obtained by the blood pressure measuring module 40. The weighting methods can be the ratio, the correlation coefficient, and the function graphics, etc., and they can also be determined by practical clinical experience.

(3) slope of the ascending branch of ABP waveform regressed by M-mode curve rising speed. The rising speed of the M-mode curve can be obtained from an M-mode image by the following equation: (end-diastolic volume−end-systolic volume)/relaxation time. The slope of the ascending branch of ABP waveform, represented by line a in FIG. 2, can be obtained by the blood pressure measuring module 40. The regression used herein refers to a statistical technique for estimating the relationships among variables.

(4) slope of the ascending branch of ABP waveform regressed by aortic forward blood flow velocity. The aortic forward blood flow velocity can be calculated according to an aortic forward blood flow Doppler signal, and the slope of the ascending branch is previously defined in (3).

(5) X-axis intercept (Vop) of left ventricular end-systolic pressure-volume relation line. Vop represents the X-axis intercept of the left ventricular end-systolic pressure-volume relation line—i.e., the left ventricular end-systolic volume when the stress is equal to zero, which can be obtained by extrapolation of multiple sets of pressure-volume data or programmed processing of a computer. In practice, the left ventricular end-systolic pressure and the left ventricular end-systolic pressure-volume relation can be obtained by left ventricular pressure measured directly from cuff blood pressure and left heart catheterization. The results show that there is an excellent correlation between the left ventricular end-systolic pressure (Pes) and mean arterial blood pressure (Bp) with r=0.82. Compared to end-systolic pressure-volume relation (ESPVR) calculated invasively from directly measured pressure, there is a better correlation with r=0.99 when using Bp to substitute left ventricular end-systolic pressure to calculate the ESPVR. Therefore, the left ventricular end-systolic pressure-volume relation line can be estimated using the mean arterial blood pressure instead of the end-systolic left ventricular pressure. The end-systolic left ventricular pressure (Pes) can be calculated as follows: Pes=(Pps−Pd)/3+Pd, where Pps is systolic pressure, and Pd is diastolic pressure, both of which can be obtained by the blood pressure measuring module 40.

(6) systolic maximum elastance (E max). Regarding the left ventricle as an oval elastomer with a posterior wall cavity, E max can be calculated according to myocardial mechanics as follows: E max=Pes/(Ves−Vop), where Pes is end-systolic left ventricular pressure; Ves is left ventricular end-systolic volume; and Vop is the X-axis intercept of the left ventricular end-systolic pressure-volume relation line. E max is a sensitive indicator that can reflect ventricular contractility and is not affected by factors such as load.

The display module 80 is coupled to the processing module 60 for displaying the blood pressure parameter, the blood flow parameter, and the myocardial mechanic parameter. Specifically, the display module 80 has: (1) an image display mode, which can be used to display a 2D ventricular motion curve, M-mode ventricular motion curve, 2D or M-mode aortic motion curve, aortic forward Doppler blood flow signal, 2D or M-mode peripheral artery motion curve, and peripheral arterial Doppler flow signal (customized by the user); (2) a parameter display mode, which can be used to display multi-site blood flow parameters and waveforms, blood pressure values and waveforms, ventricular diameter, M-mode curve rising speed and acceleration value and trend, and systolic maximum elastance (E max); (3) a mode for displaying the peripheral arterial pressure-ventricular volume diagram (systolic period); and (4) a mode for synchronously displaying the blood flow status of the left ventricle, aorta and peripheral arteries, and peripheral vascular members. The left ventricle, aorta and peripheral arteries can be displayed by 2D ultrasound (i.e., B-mode), M-mode ultrasound, ultrasound Doppler, or even 3D images. The peripheral vascular members can be displayed by 2D ultrasound, M-mode ultrasound, or ultrasound Doppler via ultra-high frequency linear array. Oxygen saturation (SpO2) can also be displayed by oximeter module. The user can freely choose which parts to be displayed, or by which displaying means. Therefore a synchronous, coupling displaying mechanism can be provided for the completed circulatory system of left ventricle-aorta-peripheral arteries-peripheral circulation.

In one embodiment, the ultrasonic medical monitoring device 100 further includes an operation panel 82 configured to receive a trigger signal. The display module 80 can display a plurality of display windows, which are switchable for displaying numerical parameters, a waveform, and a trend graph upon triggering of the operation panel 82. The "triggering" used herein can be achieved by pressing physical operation keys or touch buttons on a display screen integrated to the display module 80. In other words, by touching the operation keys or choosing corresponding touch buttons, different information, such as ultrasound images, can be displayed on the display screen of the display module 80, thus facilitating reviewing by the doctor.

In one embodiment, the ultrasonic medical monitoring device 100 further includes a storage module 50 configured to store the blood pressure parameter and the blood flow parameter, such that the doctor can access those parameters at any time.

In one embodiment, the ultrasonic medical monitoring device 100 further includes a general physiological monitoring module 90 configured to monitor general physiological parameters. The general physiological parameters include, for instance, electrocardiogram (ECG) parameters, oxygen saturation parameters, respiration, etc. Specifically, the general physiological monitoring module 90 is a functional module which can monitor at least one of said parameters; for example, it can be a module integrated with an ECG monitoring function, oxygen saturation parameters monitoring, and respiratory monitoring. The general physiological monitoring module 90 can be coupled to the processing module 60, and the physiological parameters obtained by monitoring can be displayed on the display window of the display module 80.

It should be understood that the plurality of ultrasonic probes 20, the blood pressure measuring module 40, and the general physiological monitoring module 90 can also be independent and detachable modules, which can be coupled to the monitoring host 70 via pluggable connectors. Corresponding pluggable interfaces can be reserved on the monitoring host 70, such that when using one or some of the monitoring modules, the corresponding measuring modules can be plugged to the monitoring host 70, thus facilitating choice of modules by doctors.

Compared with the conventional cardiac catheterization, the foregoing device and method acquire the blood pressure parameter and the blood flow parameter using ultrasound and a blood pressure synchronous detection technique, and the myocardial mechanics parameters, such as the systolic maximum elastance, are calculated by a computer program;

therefore the device and method will be less invasive to the human body and are suitable for clinical application.

Figure 3:
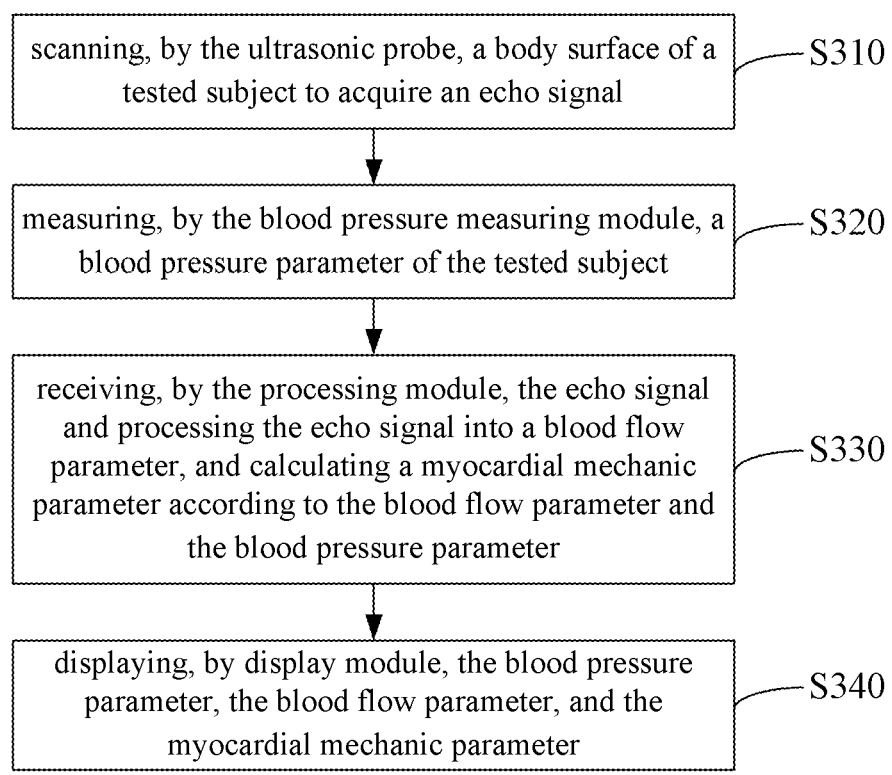
FIG. 3 is a flowchart of an embodiment of an ultrasound medical monitoring method.

Referring to FIG. 3, an ultrasonic medical monitoring method according to an embodiment can be implemented on the foregoing ultrasonic medical monitoring device. The method includes the following steps:

In step S310, a body surface of a tested subject is scanned by the ultrasonic probe to acquire an echo signal.

In one embodiment, a plurality of ultrasonic probes are attached to different portions of a body surface of a tested subject (e.g., a human), such that a longtime, stable continuous ultrasound scan monitoring sections of different parts can be achieved.

In one embodiment, the plurality of ultrasonic probes are attached to the ventricle, aorta and peripheral arteries of the tested subject to perform synchronized real-time scanning.

In step S320, a blood pressure parameter of the tested subject is measured by the blood pressure measuring module.

In one embodiment, the blood pressure measuring module is selected from the group consisting of: aneroid sphygmomanometer, finger sphygmomanometer, arterial catheter, and venous catheter tube.

In one embodiment, the blood pressure parameter includes peripheral arterial pulse wave information and blood pressure information.

In one embodiment, the blood pressure information includes a systolic pressure, a diastolic pressure, and a mean arterial pressure.

In step S330, the echo signal is received by the processing module, the echo signal is processed into a blood flow parameter, and a myocardial mechanic parameter is calculated according to the blood flow parameter and the blood pressure parameter.

In one embodiment, the step of processing the echo signal by the processing module includes: digitally processing the echo signals to obtain a digital processing signal, and obtaining a numerical parameter, waveform or trend graph calculation according to the digital processing signal, wherein the digital processing signal is selected from the group consisting of: RF signal, baseband signal, and envelope signal.

In one embodiment, the step of processing the echo signal by the processing module includes: digitally processing the echo signals to obtain a digital processing signal, obtaining an ultrasound image according to the digital processing signal and a chosen imaging mode, and obtaining the blood flow parameter calculation according to the ultrasound image, wherein the imaging mode supported by the processing module is selected from the group consisting of: B-mode imaging mode, M-mode imaging mode, color imaging mode, pulsed-wave imaging mode, elastosonography mode, 3D imaging mode, and 4D imaging mode.

In one embodiment, the blood flow parameter includes at least one of 2D ventricular motion curve, M-mode ventricular motion curve, 2D or M-mode aortic motion curve, aortic forward Doppler blood flow signal, 2D or M-mode peripheral artery motion curve, and peripheral arterial Doppler flow signal.

In one embodiment, the processing module is configured to obtain at least one selected from the group consisting of: cardiac ejection fraction, left ventricular fractional shortening, stroke volume, cardiac output, cardiac index, left ventricular end-diastolic volume, and left ventricular end-systolic volume, which are calculated according to the blood flow parameter.

In one embodiment, the processing module is configured to obtain at least one selected from the group consisting of: ventricular diameter, ventricular volume, M-mode curve rising speed and acceleration, which are calculated according to the blood flow parameter.

In one embodiment, the myocardial mechanic parameter is at least one selected from the group consisting of: duration from aortic valve closure to starting point of ABP waveform ascending branch, aortic waveform variability weighed by ventricle SV variability, slope of the ascending branch of ABP waveform regressed by M-mode curve rising speed, slope of the ascending branch of ABP waveform regressed by aortic forward blood flow velocity, X-axis intercept of the left ventricular end-systolic pressure-volume relation line, and systolic maximum elastance.

In one embodiment, the systolic maximum elastance is calculated by the following formula: E max=Pes/(Ves−Vop), where E max is the systolic maximum elastance; Pes is the end-systolic left ventricular pressure; Ves is the left ventricular end-systolic volume; and Vop is the X-axis intercept of the left ventricular end-systolic pressure-volume relation line.

In step S340, the blood pressure parameter, the blood flow parameter, and the myocardial mechanic parameter are displayed by a display module.

In one embodiment, the display module is configured to display a plurality of display windows, and the plurality of display windows are switchable for displaying numerical parameters, a waveform, and a trend graph upon triggering of the operation panel.

In one embodiment, the method further includes storing the blood pressure parameter and the blood flow parameter by a storage module.

It should be understood that embodiments of the invention may be implemented in hardware, firmware, software, or any combination thereof. Embodiments of the invention may also be implemented as instructions stored on a computer-readable storage medium, which may be read and executed by one or more processors. The computer-readable storage medium may include magnetic disk storage media, optical storage media, read only memory (ROM), random access memory (RAM), and the like. It should be understood that when an element is referred to as being "connected" or "coupled" to another element, it can be directly connected or coupled to the other element, or intervening elements may be present. It should be understood that, although the ultrasonic medical monitoring device is defined herein, the ultrasonic probes and the blood pressure measuring module can also be integrated into other medical equipment or systems, such as computed tomography (CT) or magnetic resonance imaging (MRI) equipment.

Although the description is illustrated and described herein with reference to certain embodiments, the description is not intended to be limited to the details shown. Modifications may be made in the details within the scope and range equivalents of the claims.

What is claimed is:

1. An ultrasonic medical monitoring device, comprising:
   at least one ultrasonic probe that scans a test subject to acquire an echo signal;
   a blood pressure measuring device that measures a blood pressure parameter of a peripheral artery of the test subject;
   a processor configured to receive the echo signal and process the echo signal to obtain a blood flow parameter, and to calculate a myocardial mechanic parameter that represents a synchronous coupling of a circulatory system of left ventricle-aorta-peripheral arteries circulation according to the blood flow parameter and the blood pressure parameter; and a display device that is coupled to the processor and displays the myocardial mechanic parameter;

wherein the myocardial mechanic parameter is selected from a group consisting of a slope of an ascending branch of an arterial blood pressure (ABP) waveform regressed by a M-mode curve rising speed and a slope of ascending branch of the ABP waveform regressed by an aortic forward blood flow velocity.

2. The ultrasonic medical monitoring device according to claim 1, wherein the blood pressure parameter comprises a peripheral arterial pulse wave information and a blood pressure information.

3. The ultrasonic medical monitoring device according to claim 1, wherein the ultrasonic medical monitoring device comprises a plurality of ultrasonic probes attached to different portions of the body surface of the test subject.

4. The ultrasonic medical monitoring device according to claim 3, wherein the plurality of ultrasonic probes are respectively attached to a ventricle, an aorta and a peripheral artery of the test subject to perform a synchronized real-time scanning.

5. The ultrasonic medical monitoring device according to claim 1, wherein the blood flow parameter comprises at least one of a 2D ventricular motion curve, a M-mode ventricular motion curve, a 2D or M-mode aortic motion curve, an aortic forward Doppler blood flow signal, a 2D or M-mode peripheral artery motion curve, and a peripheral arterial Doppler flow signal.

6. The ultrasonic medical monitoring device according to claim 1, further comprising an operation panel configured to receive a trigger signal; wherein, the display device is further configured to display a plurality of display windows, and the plurality of display windows are switchable for displaying a numerical parameter, a waveform and a trend graph upon triggering to the operation panel.

7. The ultrasonic medical monitoring device according to claim 1, wherein the blood pressure measuring device is selected from a group consisting of an aneroid sphygmomanometer, a finger sphygmomanometer, an arterial catheter and a venous catheter tube.

8. The ultrasonic medical monitoring device according to claim 1, further comprising a general physiological monitoring device that is coupled to the processor and configured to monitor a general physiological parameter, wherein the general physiological parameter comprises at least one of an electrocardiogram parameter and an oxygen saturation parameter.

9. An ultrasonic medical monitoring method implemented in an ultrasonic medical monitoring device, comprising:

scanning, via an ultrasonic probe, a test subject to acquire an echo signal;

measuring, via a blood pressure measuring device, a blood pressure parameter of a peripheral artery of the test subject;

receiving, via a processor, the echo signal and processing the echo signal to obtain a blood flow parameter, and calculating a myocardial mechanic parameter that represents a synchronous coupling of a circulatory system of left ventricle-aorta-peripheral arteries circulation according to the blood flow parameter and the blood pressure parameter; and displaying, via a display device, the myocardial mechanic parameter, wherein the myocardial mechanic parameter is selected from a group consisting of a-slope of an ascending branch of an arterial blood pressure (ABP) waveform regressed by a M-mode curve rising speed and a slope of ascending branch of the ABP waveform regressed by an aortic forward blood flow velocity.

10. The method according to claim 9, wherein the blood pressure parameter comprises a peripheral arterial pulse wave information and a blood pressure information.

11. The method according to claim 9, wherein the ultrasonic medical monitoring device comprises a plurality of ultrasonic probes attached to different portions of the body surface of the test subject.

12. The method according to claim 11, wherein the plurality of ultrasonic probes are respectively attached to a ventricle, an aorta and a peripheral artery of the test subject to perform a synchronized real-time scanning.

13. The method according to claim 11, wherein the blood flow parameter comprises at least one of a 2D ventricular motion curve, a M-mode ventricular motion curve, a 2D or M-mode aortic motion curve, an aortic forward Doppler blood flow signal, a 2D or M-mode peripheral artery motion curve and a peripheral arterial Doppler flow signal.

14. The method according to claim 11, wherein, the display device is configured to display a plurality of display windows, and the plurality of display windows are switchable for displaying a numerical parameter, a waveform and a trend graph upon triggering to the operation panel.

15. The ultrasonic medical monitoring device according to claim 11, further comprising: monitoring, by a general physiological monitoring device, a general physiological parameters, wherein the general physiological parameter comprises at least one of an electrocardiogram parameter and an oxygen saturation parameter.

* * * * *